United States Patent
Cairns et al.

(10) Patent No.: US 8,697,718 B2
(45) Date of Patent: Apr. 15, 2014

(54) PACK OF MEDICINAL TABLETS

(75) Inventors: Graham Cairns, Hull (GB); John Alfred Davis, Hull (GB); Neil Hyde, Hull (GB)

(73) Assignee: RB Pharmaceuticals Limited, Slough, Berkshire (GB)

( * ) Notice: Subject to any disclaimer, the term of this patent is extended or adjusted under 35 U.S.C. 154(b) by 0 days.

(21) Appl. No.: 12/664,285

(22) PCT Filed: May 14, 2008

(86) PCT No.: PCT/GB2008/001659
§ 371 (c)(1),
(2), (4) Date: Jul. 6, 2010

(87) PCT Pub. No.: WO2008/152347
PCT Pub. Date: Dec. 18, 2008

(65) Prior Publication Data
US 2010/0292265 A1    Nov. 18, 2010

(30) Foreign Application Priority Data
Jun. 13, 2007    (GB) .................................. 0711376.4

(51) Int. Cl.
*A61K 31/485*    (2006.01)
*B65D 83/04*    (2006.01)
*B65B 31/02*    (2006.01)

(52) U.S. Cl.
USPC .............. 514/279; 206/531; 206/540; 53/432

(58) Field of Classification Search
None
See application file for complete search history.

(56) References Cited

U.S. PATENT DOCUMENTS

| 5,614,555 | A | * | 3/1997 | Nakai et al. | 514/540 |
| 5,911,325 | A | * | 6/1999 | Breitler | 206/539 |
| 2002/0132359 | A1 | * | 9/2002 | Waterman | 436/127 |
| 2003/0021752 | A1 | * | 1/2003 | Whittle et al. | 424/45 |
| 2003/0138503 | A1 | * | 7/2003 | Staniforth et al. | 424/725.1 |
| 2006/0025383 | A1 | * | 2/2006 | Wishart et al. | 514/63 |
| 2006/0183804 | A1 | * | 8/2006 | Brinkman et al. | 514/567 |
| 2007/0049640 | A1 | * | 3/2007 | Pavliv | 514/562 |

FOREIGN PATENT DOCUMENTS

EP    0656389    * 10/2001

* cited by examiner

*Primary Examiner* — Robert A Wax
*Assistant Examiner* — Randeep Singh
(74) *Attorney, Agent, or Firm* — Troutman Sanders LLP; Ryan A. Schneider; Troy S. Kleckley

(57) ABSTRACT

A water- and oxygen-occlusive pack is described. The pack encloses an inert atmosphere containing medicinal tablets, wherein the tablets contain buprenorphine or a salt or ester thereof.

11 Claims, No Drawings

PACK OF MEDICINAL TABLETS

BENEFIT CLAIMS

This application is a US National Stage of International Application No. PCT/GB2008/001659, filed 14 May 2008, which claims the benefit of GB 0711376.4, filed 13 Jun. 2007.

FIELD OF THE INVENTION

This invention relates to a pack of medicinal tablets, in particular to a pack of medicinal tablets containing buprenorphine or a salt or ester thereof, as the, or an, active ingredient.

BACKGROUND OF THE INVENTION

Existing products containing buprenorphine hydrochloride are TEMGESIC (trade mark), SUBUTEX (trademark) and SUBOXONE (trade mark); products sold for the treatment of moderate to severe pain or for the treatment of opiate addiction. TEMGESIC and SUBUTEX contain buprenorphine hydrochloride as the sole active ingredient; SUBOXONE contains buprenorphine hydrochloride and naloxone, as co-active ingredients.

It has been stated in WO 2005/117838 that buprenorphine hydrochloride shows degradation in acid or alkaline conditions and may be degraded by oxidation.

One attempt to stabilise buprenorphine is provided in U.S. Pat. No. 6,365,596, which discloses pharmaceutical compositions containing buprenorphine and at least one antioxidant in a molar ratio, antioxidant to buprenorphine, in the range 1:1 to 3:1. It is also mentioned in U.S. Pat. No. 6,365,596 that stability is improved by avoiding the presence of magnesium ions, and polyvinylpyrrolidone.

In the invention of WO 2005/117838 the improvement is to stabilise buprenorphine by using a lower concentration of an antioxidant, compared with U.S. Pat. No. 6,365,596 (preferably 1:1000-1:10, molar ratio, antioxidant: buprenorphine), and a chelating agent (preferably 0.01-5%, wt:wt).

We see an inherent undesirability in having to use a large amount of an antioxidant (per U.S. Pat. No. 6,365,596), or an antioxidant and a chelating agent together (per WO 2005/117838), in order to stabilise buprenorphine and/or salts or esters thereof.

BRIEF SUMMARY OF THE INVENTION

In accordance with a first aspect of the present invention there is provided a water- and oxygen-occlusive pack enclosing an inert atmosphere containing medicinal tablets, wherein the tablets contain buprenorphine or a salt or ester thereof.

Preferably the inert gas is nitrogen.

A traditional pack for tablets containing buprenorphine hydrochloride is a PVC/PVdC blister pack. PVC/PVdC is a laminate of polyvinyl chloride polyvinylidene chloride. It is generally accepted to be a good oxygen and moisture barrier, suitable for the packaging of many medicinal products. Nevertheless we have found that the stored tablets, and in particular the active ingredient buprenorphine hydrochloride, may be affected both by moisture and by oxygen, in such a pack.

In the present invention the use of a water- and oxygen-occlusive barrier material in combination with keeping the tablets under an inert atmosphere protects the active ingredient(s) from significant chemical decomposition.

The approach followed in the present invention is in contrast with the prior art methods of U.S. Pat. No. 6,365,596 and WO 2005/117838, which both follow the approach of seeking improvement in stability by chemical formulation improvement.

Preferably each tablet contains at least 0.2 mg buprenorphine, preferably at least 0.4 mg.

Preferably each tablet contains up to 20 mg buprenorphine, preferably up to 16 mg, preferably up to 12 mg, preferably up to 10 mg, preferably up to 8 mg, preferably up to 4 mg, preferably up to 2 mg.

These amounts referring to buprenorphine may be converted to buprenorphine salts or esters, if such forms are present, by simple arithmetical scaling.

Thus, when buprenorphine hydrochloride is present, each tablet preferably contains at least 0.21 mg of buprenorphine hydrochloride, preferably at least 0.43 mg; and preferably up to 22 mg of buprenorphine hydrochloride, preferably up to 18 mg, and more preferably up to 13 mg. In especially preferred embodiments each tablet containing buprenorphine hydrochloride contains up to 11 mg of buprenorphine hydrochloride, preferably up to 9 mg, preferably up to 4.5 mg, preferably up to 2.4 mg.

A co-active ingredient may be present. Naltrexone, nalmefene and, especially, naloxone are preferred. Preferably the weight of such co-active ingredients (or of co-active ingredients in total), does not exceed the weight of buprenorphine; and preferably is not greater than 50% wt/wt, of the weight of buprenorphine (non-salt, non-ester compounds compared). The weight ratio in the tablet of buprenorphine to such a co-active ingredient, or of co-active ingredients in total, is preferably in the range 2:1 to 8:1, preferably 3:1 to 5:1.

In these and other definitions a weight of "buprenorphine" also denotes a weight of salt or ester, converted to buprenorphine content (i.e. the base). Should there be more than one buprenorphine compound (e.g. buprenorphine and buprenorphine hydrochloride) the total weight, converted to buprenorphine, is to be used in the definition.

Preferably the tablets comprise at least one monosaccharide or disaccharide or a mixture thereof.

When a monosaccharide is present it may suitably be a sugar, for example glucose, galactose; fructose or mannose, or a sugar alcohol, for example mannitol or sorbitol. Preferably the amount of monosaccharide, or of monosaccharides in total, is in the range 15-50% wt/wt of composition, preferably 20-40% wt/wt. Sugar alcohols are preferred monosaccharides, especially mannitol.

When a disaccharide is present it may suitably be a sugar, for example maltose, lactose or sucrose. Preferably the amount of disaccharide, or of disaccharides in total, is in the range 20-70% wt/wt of composition, preferably 40-60% wt/wt. Lactose is a preferred disaccharide.

Preferably the tablets comprise a disintegrant.

When a disintegrant is present it may suitably be sodium croscarmellose, maize starch or crospovidone. Preferably the amount of disintegrant, or of disintegrants in total, is in the range 1-30% wt/wt of composition, preferably 10-20% wt/wt.

Preferably the tablets comprise a pressing aid, preferably in an amount in the range 0.1-2% wt/wt of composition. A preferred pressing aid is magnesium stearate.

Preferably the tablets comprise a mixture of anhydrous citric acid and sodium citrate, preferably in a weight ratio of 2:1 to 1:1. Preferably the total amount of anhydrous citric acid and sodium citrate is in the range 0.5-4% wt/wt of composition.

Preferably the pack has a water- and oxygen-occlusive wall material.

Preferably the pack is a blister pack having a plurality of blister pockets, each containing one tablet and each containing a charge of inert gas.

In a preferred embodiment the pack is of an aluminium or aluminium-plastics laminate having a water-occlusive and oxygen-occlusive wall material with each blister pocket containing an inert atmosphere of nitrogen gas, and one tablet.

A water-occlusive and oxygen-occlusive pack of this invention has a wall or barrier member of water-occlusive and oxygen-occlusive material. By water-occlusive and oxygen-occlusive material, we mean a material which has a higher degree of water and oxygen occlusivity under test conditions, 25° C./60% Relative Humidity (RH) and 40° C./75% RH, than a traditional PVC/PVdC material.

In a PVC/PVdC material, the PVC is believed to be the "weak link". Preferably a blister pack of the invention comprises or is formed of a metallic material, for example aluminium or an aluminium alloy. Most preferably the base part, containing the pockets for tablets, may be of a cold-formable foil, comprising a metallic layer, over which a breachable-by-tablet metallic foil is laid, to close the pack. Especially preferred is a foil comprising a layer of a metallic material, for example aluminium or aluminium alloy, laminated to a layer of aliphatic polyamide and/or a layer of PVC. Especially preferred is a foil having a layer of aliphatic polyamide, 10-40 μm thick, then a metallic layer, 30-60 μm thick, then a layer of PVC, 40-80 μm thick, the latter being the product contact surface.

The pack may be packed with tablets and sealed, in an atmosphere of the inert gas.

Preferably the blister pack contains at least 6 tablets, more preferably at least 8 tablets. Preferably the blister pack contains up to 14 tablets, especially up to 12 tablets.

The protection provided by the present invention means that there is no need to add undesirable ingredients such as chemical stabilisers, for example chelating agents or antioxidants, to the formulation of the tablet in order to improve chemical stability.

Preferably the tablets do not contain a chelating agent which stabilizes the buprenorphine or acid or salt thereof.

Preferably the tablets do not contain an antioxidant to protect the buprenorphine or acid or salt thereof.

Preferably the tablets do not contain a chelating agent to protect the buprenorphine or acid or salt thereof.

Preferably the tablets do not contain any component to protect the buprenorphine or acid or salt thereof.

The protection provided by the present invention means that there is no need to omit certain ingredients which have been implicated in causing chemical stability; for example magnesium ions or polyvinylpyrrolidone, according to U.S. Pat. No. 6,365,596. There is no necessity to exclude such compounds from the tablets in the pack of the present invention. Indeed magnesium stearate is a preferred component of the formulation for the tablets.

Preferably the pack of the invention has a use-by date at least 18 months after its date of packing; more preferably at least 24 months. The use-by date may be recorded on the pack itself or on secondary packaging.

In accordance with a second aspect there is provided a method of manufacturing a pack of the first aspect, wherein the tablets are enclosed in a water- and oxygen-occlusive material under an inert atmosphere.

In accordance with a third, aspect of the present invention there is provided a method of supplying and/or administering tablets from a water- and oxygen-occlusive pack of the first aspect.

DETAILED DESCRIPTION OF PREFERRED EMBODIMENTS

The invention will now be further described, by way of example, with reference to the following example.

Medicament tablets were made, containing the following ingredients.

| Component | Quantity/tablet (mg) | Quantity/tablet (mg) |
| --- | --- | --- |
| Buprenorphine hydrochloride | 0.216 | 0.432 |
| Lactose monohydrate | 29.842 | 29.628 |
| Mannitol | 18.000 | 18.000 |
| Maize starch | 9.000 | 9.000 |
| Povidone K30 | 1.200 | 1.200 |
| Citric acid anhydrous granular | 0.888 | 0.888 |
| Magnesium stearate | 0.450 | 0.450 |
| Sodium citrate | 0.404 | 0.404 |
| TOTAL | 60.0 | 60.0 |

The tablets were prepared as follows.

All the excipients were screened through a 20 mesh sieve screen. The lactose, starch, mannitol and povidone were thoroughly mixed together, wetted and granulated with a solution of buprenorphine hydrochloride, citric acid and sodium citrate previously dissolved in a mixture of the purified water and ethanol by stirring. The resultant granules were dried at 42-48° C. until a moisture content of 1-2% was attained. The granules were screened through a 20 mesh sieve screen and blended. Magnesium stearate was added to the sieved granules and mixed thoroughly. The granules were sieved and re-blended. The mixture was tabletted using 7/32 inch (5.6 mm) punches to a target weight of 60 mg.

The resulting tablets were packed into two types of blister pack: one in accordance with the present invention, which had a cold form aluminium foil tray, heat sealed by an aluminium breachable foil lid under an inert nitrogen atmosphere; the other a "250/60" PVC/PVdC tray (250 PVC, 60 PVdC), with an aluminium breachable foil lid. The blister packs contained seven tablets. Packing for the present invention was carried out in a dry nitrogen atmosphere in order that each blister pocket contained nitrogen gas. Packing in the PVC/PVdC blisters was carried out in dry air. Each tablet pocket was individually sealed, by the breachable aluminium foil lid. Tablets were packed into the blister trays and sealed immediately after their manufacture.

The cold-form aluminium foil tray was a laminate of 25 μm thickness aliphatic polyamide, 46 μm thickness aluminium and 60 μm thickness PVC (the product contact surface).

The aluminium breachable foil lid was a 50 g/m² lidding foil of 12 μm PET/25 μm aluminium/6-8 g/m² PVC/PVA lacquer (product contact surface).

The tablets were then stored under constant conditions of 25° C. temperature and 60% Relative Humidity (RH) and 40° C./75% RH. Samples were studied at several scheduled time points under these conditions for buprenorphine content, content of the compound we identified as being the main degradant, and total related degradation products. The results for three batches of tablets containing 0.216 mg buprenorphine hydrochloride per tablet are tabulated below. This converts to 0.2 mg buprenorphine and the tables which follow quote the buprenorphine level (i.e., 100%=0.2 mg).

| | Buprenorphine Content (% Nominal) at 25° C./60% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 98.5 | 98.0 | 99.5 | 98.5 | 99.5 | 99.0 |
| 3 | 95.0 | 94.0 | 96.0 | 97.0 | 98.0 | 97.5 |
| 6 | 92.5 | 93.5 | 94.0 | 97.5 | 98.0 | 98.5 |
| 9 | 98.0 | 97.5 | 99.0 | 103.0 | 103.0 | 104.0 |
| 12 | 94.5 | 93.5 | 94.5 | 100.0 | 103.5 | 103.5 |
| 18 | 92.0 | 93.5 | 93.5 | 101.5 | 102.5 | 99.0 |
| 24 | 90.5 | 91.0 | 90.5 | 101.5 | 103.0 | 101.5 |
| 36 | 89.0 | 88.5 | 88.5 | 102.5 | 102.0 | 103.5 |

| | Buprenorphine Content (% Nominal) at 40° C./75% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 98.5 | 98.0 | 99.5 | 98.5 | 99.5 | 99.0 |
| 1 | 96.0 | 96.0 | 96.0 | 97.0 | 97.5 | 98.5 |
| 3 | 93.5 | 93.5 | 94.0 | 96.5 | 97.0 | 97.0 |
| 6 | 89.0 | 89.5 | 90.0 | 97.0 | 98.5 | 97.5 |
| 12 | 85.5 | 83.5 | 87.5 | 100.5 | 100.5 | 101.0 |

| | Main Degradant Compound (% w/w) at 25° C./60% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 0.9 | 1.0 | 0.6 | 1.2 | 1.4 | 0.7 |
| 3 | 1.9 | 1.7 | 1.3 | 0.9 | 0.9 | 0.3 |
| 6 | 3.1 | 3.1 | 2.6 | 1.1 | 1.2 | 0.5 |
| 9 | 4.5 | 4.4 | 3.9 | 1.2 | 1.3 | 0.6 |
| 12 | 5.2 | 5.1 | 4.6 | 1.3 | 1.4 | 0.6 |
| 18 | 6.7 | 6.6 | 6.1 | 1.4 | 1.4 | 0.6 |
| 24 | 7.9 | 7.8 | 7.3 | 1.4 | 1.5 | 0.7 |
| 36 | 9.8 | 9.6 | 9.3 | 1.4 | 1.4 | 0.7 |

| | Main Degradant Compound (% w/w) at 40° C./75% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 0.9 | 1.0 | 0.6 | 1.2 | 1.4 | 0.7 |
| 1 | 2.8 | 2.7 | 2.4 | 1.4 | 1.4 | 0.7 |
| 3 | 3.5 | 3.8 | 3.3 | 1.1 | 1.1 | 0.6 |
| 6 | 6.3 | 6.4 | 5.8 | 1.3 | 1.3 | 0.7 |
| 12 | 13.8 | 13.5 | 12.7 | 1.6 | 1.5 | 0.9 |

| | Total Related Degradation Products (% w/w) at 25° C./60% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 2.4 | 2.6 | 1.8 | 2.7 | 3.0 | 1.7 |
| 3 | 3.4 | 3.2 | 2.7 | 1.8 | 1.7 | 0.9 |
| 6 | 6.2 | 6.2 | 5.6 | 2.6 | 2.7 | 1.5 |
| 9 | 8.8 | 8.5 | 7.9 | 2.9 | 3.0 | 1.8 |
| 12 | 9.7 | 9.4 | 8.9 | 2.9 | 3.1 | 1.8 |
| 18 | 12.2 | 12.2 | 11.6 | 3.1 | 3.1 | 1.9 |
| 24 | 14.5 | 14.4 | 13.6 | 3.4 | 3.5 | 2.3 |
| 36 | 17.3 | 17.0 | 16.6 | 3.1 | 3.1 | 2.2 |

| | Total Related Degradation Products (% w/w) at 40° C./75% RH Nominal = 0.2 mg/tablet | | | | | |
|---|---|---|---|---|---|---|
| Time | PVC/PVdC | | | Alu/N$_2$ | | |
| (Months) | 1 | 2 | 3 | 1 | 2 | 3 |
| 0 | 2.4 | 2.6 | 1.8 | 2.7 | 3.0 | 1.7 |
| 1 | 3.9 | 3.8 | 3.5 | 2.3 | 2.2 | 1.4 |
| 3 | 5.1 | 5.4 | 4.8 | 2.2 | 2.1 | 1.3 |
| 6 | 9.1 | 9.2 | 8.4 | 2.6 | 2.6 | 1.7 |
| 12 | 18.7 | 17.9 | 16.9 | 2.6 | 2.5 | 1.8 |

The results for the tablets packed in the PVC/PVdC blister pack show clear evidence of chemical decomposition (or oxidation) of the active ingredient, buprenorphine. There is a clear time and temperature-dependent decrease in buprenorphine content upon storage. Moreover, there are corresponding time and temperature-dependent increases in the levels of the main degradant compound and of total buprenorphine-related degradation products.

The results for the tablets packed in aluminium blisters under nitrogen gas do not demonstrate any clear evidence of chemical decomposition (or oxidation) of the active ingredient upon storage for 36 months at 25° C./60% RH or for 12 months at 40° C./75% RH. There is no time or temperature-dependent decrease in buprenorphine content and no time or temperature-dependent increase in levels of degradation products.

Chemical decomposition of the active ingredient is clearly shown in the tablets of the PVC/PVdC pack, but not in the tablets of the Alu/N$_2$ pack.

The protection for chemical decomposition provided by the present invention means that there is no need to add undesirable ingredients such as chemical stabilisers or antioxidants to the formulation of the tablet in order to improve chemical stability.

What is claimed is:

1. A water- and oxygen-occlusive blister pack enclosing an inert atmosphere storing medicinal tablets, the pack comprising:

a breachable-by-tablet foil; and a water- and oxygen-occlusive wall in communication with the breachable-by-tablet foil to enclose the inert atmosphere therebetween, the water- and oxygen-occlusive wall comprising a metal and plastic laminate, the laminate comprising a 30-60 μm thick layer of metallic material laminated to a layer of one or both of aliphatic polyamide and polyvinyl chloride, the laminate further protecting the stored tablets from significant chemical decomposition;

wherein the tablets contain buprenorphine or a salt or ester thereof and a mixture of anhydrous citric acid and sodium citrate;

wherein the tablets do not contain either an antioxidant or a chelating agent due to the water- and oxygen-occlusive wall that protects the tablets from significant chemical decomposition;

wherein the laminate consists of a 10-40 μm thick layer of the aliphatic polyamide distal to at least one tablet, and a 40-80 μm thick layer of the polyvinyl chloride in proximity to the at least one tablet; and wherein the breachable-by-tablet foil consists of about 50 g/m² lidding foil consisting of a lacquer consisting of about a 12 μm thick layer of polyethylene terephthalate, about a 25 μm thick layer of aluminum and about 6-8 g/m² polyvinyl chloride/polyvinyl alcohol, the polyvinyl chloride/polyvinyl alcohol in proximity to the at least one tablet.

2. A water- and oxygen-occlusive pack as claimed in claim 1, wherein the tablets comprise from 0.2 to 20 mg of buprenorphine or a scaled amount of a salt or ester thereof.

3. A water- and oxygen-occlusive pack as claimed in claim 1, wherein each tablet thereof contains from 0.21 mg to 22 mg of buprenorphine hydrochloride.

4. A water- and oxygen-occlusive pack as claimed in claim 1, wherein the tablets include a monosaccharide or a disaccharide or a mixture thereof.

5. A water and oxygen-occlusive pack as claimed in claim 1, wherein the tablets comprise lactose.

6. A water and oxygen-occlusive pack as claimed in claim 1, wherein the tablets comprise mannitol.

7. A water and oxygen-occlusive pack as claimed in claim 1, wherein the tablets comprise a disintegrant.

8. A water and oxygen-occlusive pack as claimed in claim 1, wherein the tablets comprise magnesium stearate.

9. A method of supplying and/or administering tablets from a water- and oxygen-occlusive pack as claimed in claim 1.

10. A water- and oxygen-occlusive pack as claimed in claim 1, wherein the tablets have a use-by date at least 18 months after their packing under an inert nitrogen atmosphere into the water- and oxygen-occlusive pack.

11. A water- and oxygen-occlusive pack as claimed in claim 1, wherein the metal and plastic laminate of the water- and oxygen-occlusive wall comprises a layer of aluminium or alloy thereof laminated to a layer of one of both of aliphatic polyamide and PVC.

* * * * *